(12) United States Patent
Bartuschat et al.

(10) Patent No.: US 12,087,436 B2
(45) Date of Patent: Sep. 10, 2024

(54) MEDICAL TECHNOLOGY FACILITY, METHOD FOR OPERATING A MEDICAL TECHNOLOGY FACILITY, COMPUTER PROGRAM, AND ELECTRONICALLY READABLE DATA CARRIER

(71) Applicant: Siemens Healthcare GmbH, Erlangen (DE)

(72) Inventors: Dominik Bartuschat, Hofheim (DE); Markus Mellgren, Forchheim (DE); Roland Stenzel, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/371,966

(22) Filed: Sep. 22, 2023

(65) Prior Publication Data
US 2024/0112796 A1 Apr. 4, 2024

(30) Foreign Application Priority Data
Sep. 29, 2022 (DE) ..................... 10 2022 210 350.5

(51) Int. Cl.
*A61B 6/00* (2024.01)
*G06T 1/00* (2006.01)
*G16H 40/40* (2018.01)

(52) U.S. Cl.
CPC ............. *G16H 40/40* (2018.01); *A61B 6/547* (2013.01); *G06T 1/0007* (2013.01)

(58) Field of Classification Search
CPC ........ G16H 40/40; A61B 6/547; G06T 1/0007
See application file for complete search history.

(56) References Cited

U.S. PATENT DOCUMENTS

2017/0220709 A1* 8/2017 Wan ..................... A61N 5/1048

FOREIGN PATENT DOCUMENTS

| DE | 10200534 A1 | 7/2003 |
|---|---|---|
| DE | 112017000642 T5 | 11/2018 |

* cited by examiner

*Primary Examiner* — Dani Fox
(74) *Attorney, Agent, or Firm* — Lempia Summerfield Katz LLC

(57) ABSTRACT

A medical technology facility includes a functional component, a carrier arrangement provided so as to position the functional component in a space, at least one additional component configured to be positioned and/or formed differently in different positions of the carrier arrangement, and a control facility. In order to form a collision protection system, the control facility is configured to: update a digital movement model of the medical technology facility, wherein the digital movement model maps the carrier components and the functional component with their movability based on position data that indicates prevailing positions of the carrier components; evaluate the prevailing movement model so as to detect possibly impending collisions with at least one subject and/or object that is located in the movement region and that is mapped in the movement model; and implement at least one collision protection measure when an impending collision is detected.

13 Claims, 4 Drawing Sheets

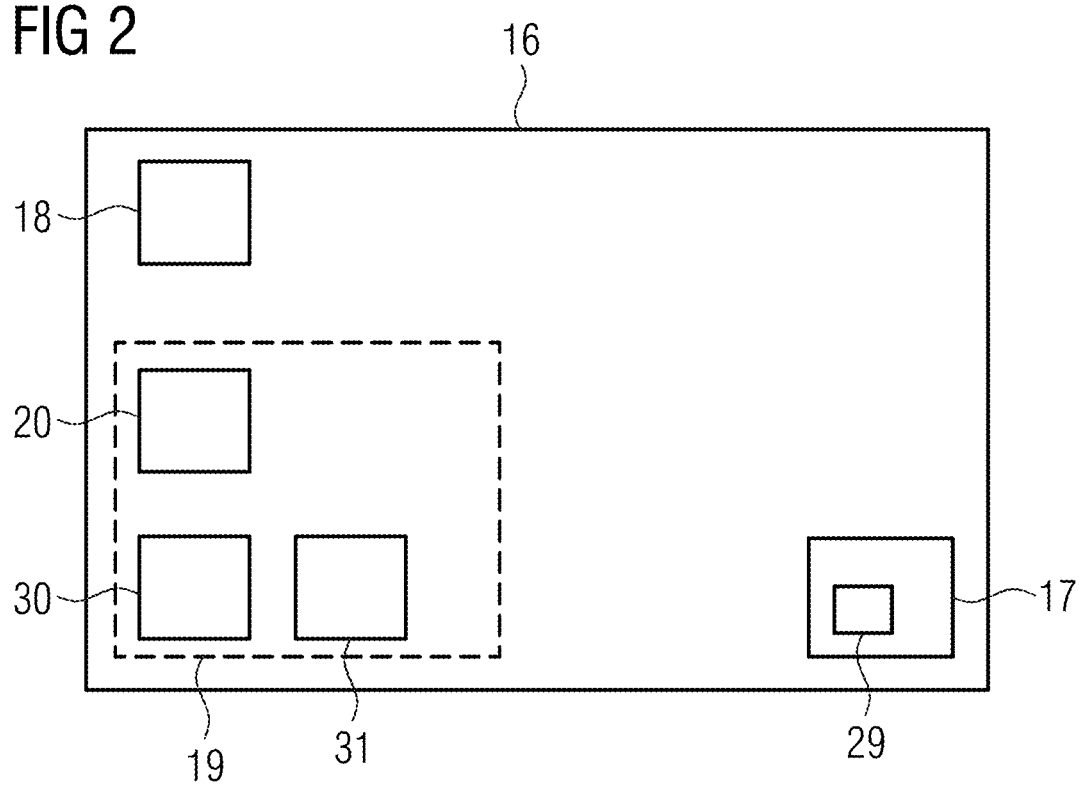

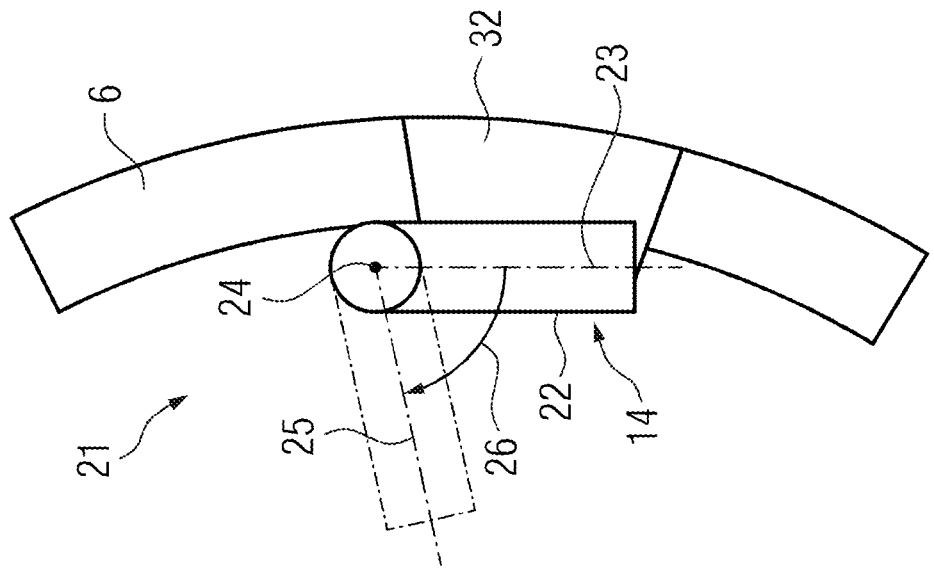
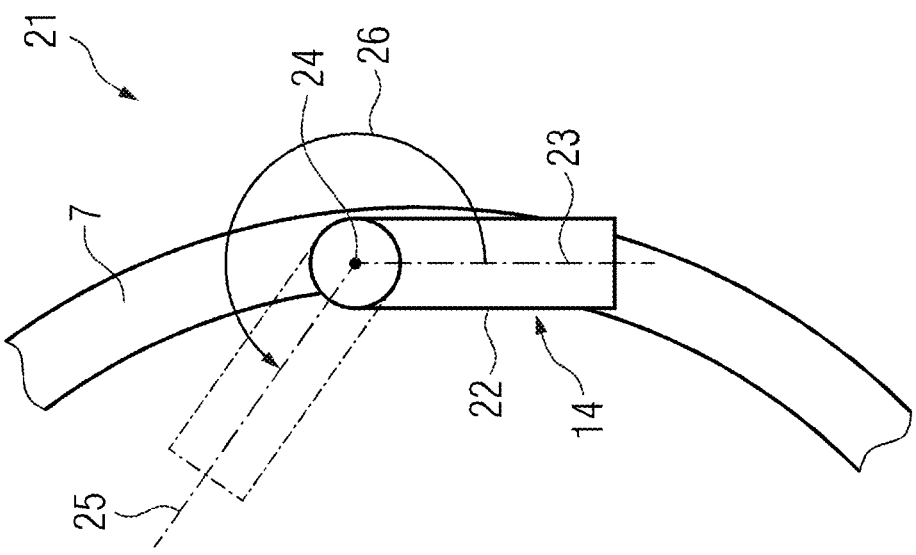

ously monitor the move-
MEDICAL TECHNOLOGY FACILITY, METHOD FOR OPERATING A MEDICAL TECHNOLOGY FACILITY, COMPUTER PROGRAM, AND ELECTRONICALLY READABLE DATA CARRIER The present patent document claims the benefit of German Patent Application No. 10 2022 210 350.5, filed Sep. 29, 2022, which is hereby incorporated by reference in its entirety.

TECHNICAL FIELD

The disclosure relates to a medical technology facility, a computer-implemented method for operating such a medical technology facility, a computer program, and an electronically readable data carrier.

BACKGROUND

Medical technology facilities, in particular such medical technology facilities for examining and treating a patient, frequently have movable components for which it is desired that they do not collide with the patient or other detectable objects, e.g., further components of the medical technology facility. Such a medical technology facility may have at least one functional component that may be positioned via a carrier arrangement, which has a carrier component, in the space so as to correctly examine and/or treat the patient. Such a functional component in the case of a medical imaging facility may be a recording arrangement. In the case of a radiotherapy facility, the functional component may be a radiation head or the like.

This issue is particularly relevant for X-ray facilities that have a recording arrangement that have an X-ray emitter and an X-ray detector and that may be freely positioned in the space. In this case, different projection directions or recording geometries may be performed that are coordinated to the medical procedure to be performed. X-ray facilities of this type may have a C-arm, wherein the X-ray emitter and the X-ray detector are arranged lying opposite one another on the C-arm. The C-arm in this case forms a carrier component. The C-arm may be held in a displaceable manner, for example, so as to realize an orbital rotation as a degree of freedom of movement in an outer arm by a holder (e.g., a carriage) that form further carrier components. The outer arm is also in part referred to as a (e.g., outer) telescopic C-arm, wherein the actual C-arm is referred to as the inner C-arm. Other embodiments of such X-ray facilities having a C-arm and also attachments that move the X-ray emitter and X-ray detector may also include robot arms. X-ray facilities of this type may also be referred to as angiography systems, (e.g., robotic angiography systems), and may also be used in the case of minimally invasive interventions to patients, e.g., during clinical interventions.

For medical technology facilities, due to collision protection systems, the more conservatively these are designed, the more the freedom of movement may be limited for the functional component. This means that specific treatment positions and/or examination positions, for example, recording geometries in the case of imaging facilities, possibly cannot be achieved on account of the collision protection system, although these specific treatment positions and/or examination positions may be achievable in the case of a more precise effect of the collision protection system. A high cost factor and a high outlay, which means a high degree of complexity, may stand in the way of highly precise collision protection systems that maximize the freedom of movement.

Thus, collision protection systems are already proposed that use distance sensors on the functional component and/or the carrier components of the carrier arrangement, which are however costly and highly complex with regard to installation, the data evaluation, and the underlying control. Therefore, software-based collision protection systems, which, for example, in a control facility of the medical technology facility readily use existing position data of the carrier components, may be implemented as more cost-efficient and in a simpler manner. Software-based collision protection systems moreover render it possible to perform a more rapid movement of the carrier components relative to one another by avoiding dead angles that are produced, for example, due to sterile covers and are even capable of assessing penetration depth to render possible rapid resolution of collision situations.

For example, collision protection systems are proposed that, by a movement model, continuously monitor the movement of the medical technology facility and prevent collision-related risks by limiting system speeds. In order to calculate spacing, the medical technology facility may be deconstructed in the movement model into a limited number of rigid geometric elements and their spatial poses, (e.g., positions and orientations), may be acquired in the movement model by a kinematic chain. In addition to the medical technology facility, further objects and/or subjects may also be detected in the movement model, in particular objects and/or subjects with which a collision is not desired. This relates in many implementations mainly to the patient as the subject.

For cost reasons and in order to reduce the complexity, the movement models may only have the degrees of freedom of movement of the carrier arrangement that are in direct relation to the positioning of the patient and the functional component are mapped. These degrees of freedom of movement have the advantage that the encoders of the actuators that are used accordingly for moving the carrier components may already provide sufficient position data. This however leads to the problem that some additional components of the medical technology facility, (e.g., cable routing components having rotatable cable outlets), namely as the carrier arrangement is being altered at least in part change their pose and/or shape however may not be reproduced in the movement model since in this regard position data is not available. Accordingly, it is proposed to map additional components of this type by enlarged geometric model elements of the additional components that cover the entire feasible freedom of movement of the additional component. Such enlarged "blown up" model elements are however disadvantageous because clinically relevant positions possibly cannot be reached or cannot be reached at least within the shortest possible time.

SUMMARY AND DESCRIPTION

The object of the disclosure is therefore to provide a collision protection concept that increases the available positioning free space for functional components and that nevertheless robustly prevents collisions.

This object is achieved in accordance with the disclosure by a medical technology facility, a method, a computer program, and an electronically readable data carrier, as disclosed herein. The scope of the present disclosure is defined solely by the appended claims and is not affected to any degree by the statements within this summary. The present embodiments may obviate one or more of the drawbacks or limitations in the related art.

In the case of a medical technology facility of the type mentioned in the introduction, it is provided in accordance with the disclosure that the movement model also maps the movement of the additional component, wherein the modelling unit is configured so as to determine additional data, which describes a prevailing pose and/or shape of the additional component, from a relationship, which is stored in the control facility, of at least one part of the position data with the additional data.

One underlying finding of the disclosure is that a deterministic relationship may exist between the movement of the carrier components and the additional component that is in particular connected thereto and the relationship is utilized in order to incorporate the additional component at least in part into the movement model and to map the movement of the additional component so that it is possible to avoid enlarged geometric elements, which represent blocked space. Consequently, in addition to an improved protection of subjects and/or objects that are to be kept safe from collision, the improved movement model provides an increased freedom of movement so that an examination and/or treatment by the functional component may be performed in a greater range of clinically relevant positions, which therefore may improve the quality of the examination and/or treatment, in particular of medical interventions. In this case, as is described in greater detail below, the improvements may be made using elements of the collision system that are already provided, in particular of the movement model, without a fundamental change of the existing software structure being required. In particular, an additional complex and/or expensive additional sensor system related to the additional component is not required.

The improved design in accordance with the disclosure of the software-based collision protection system solves limitations of the freedom of movement with regard to clinically relevant positions that exist on account of the lack of safety with regard to the pose (position and orientation) and/or shape of the additional components in that deterministic relationships between the movement of the additional component and the position data that is already provided are used. Due to this fundamental improvement, the previously used, enlarged model elements may be replaced by more precise geometric representations and poses/shapes so that the ability to reach clinically relevant regions of interest may be broadened without the necessity for the introduction of complex and costly position sensors. The disclosure also renders it possible to more rapidly position the functional component since the actual geometry is reproduced and the shortest collision-free movements are rendered possible.

In this case, the at least one additional component may include at least one element of a cable routing component for at least one cable to the functional component. In order to be able to perform its function, functional components may require at least one cable feed, for example, a supply of electrical and/or other power and/or at least one data line/communication line. Despite the carrier arrangement having its carrier components that may be moved relative to one another, it is necessary to feed the corresponding cable to the functional component. For this purpose, cable routing components that have a specific movability may be used between at least two of the carrier components. If the carrier components are moved, the pose and/or shape of the cable routing component and its elements is therefore changed. In this case, the at least one element of the cable routing component that is taken into consideration as an additional component in the movement model on the basis of the relationship may be at least one rigid cable outlet, in particular for connecting to a grooved hose/corrugated tube. For example, cable routing components may have two cable outlets that are rotatably attached in each case to one carrier component and the cable outlets are flexibly connected via a grooved hose and also where necessary in a length-adaptable manner. In this case, the cable outlets may be mapped in their ability to rotate as additional components in the movement model, wherein a more complex integration of the grooved hose may also be avoided.

The reason for this is that in practice and in experiments it has been shown that collision problems tend to originate from the cable outlets but not from the grooved hose, meaning that a modelling of the cable outlets, which is in particular simple to implement, is sufficient for a clear improvement in quality of the movement model and consequently an increased freedom of movement for the functional component. In this case, exemplary embodiments are feasible in which the additional component, which represents the cable outlet in the movement model, is longer than the cable outlet in reality with the result that a part of the grooved hose may also still be mapped over this in order to achieve a further improvement.

In the example of the cable outlet as a (rotatable) additional component, the additional component may be added to the movement model that uses at least one kinematic chain in Denavit-Hartenberg notation (DH notation), in particular as a rigid, rotatably coupled kinematic element. Via a kinematic chain, it is possible to easily map the carrier arrangement in a particularly computationally efficient, low cost, and simple to manage manner in the movement model. It is proposed to maintain this fundamentally simple construction of rigid kinematic elements, which are in particular rotationally coupled to one another, of the kinematic chain even when adding the at least one additional component and to add this to the kinematic chain in the DH notation that may be used here. In the case of coupling as a rigid, rotatably coupled kinematic element, which represents the cable outlet as an element of the cable routing component in the movement model, the additional data then may describe an angular position of the at least one kinematic element (and consequently the cable outlet). This angular position may be understood as an exit angle of the cable. In particular, the additional data may describe at least one angular position of a respective kinematic element (model element) of the additional component with respect to a carrier component and/or functional component that is connected to the element. In the case of cable outlets as additional components and rigid kinematic elements that are rotatably coupled in each case to one carrier component, it is possible therefore to define a zero position for the angle of the angular position, wherein then the relationship renders it possible to determine the corresponding angle from at least one part of the position data. If the cable routing component connects to two carrier components that are in particular adjacent in the kinematic chain and are connected via the kinematic chain, in particular the item of position data, which describes the position of these carrier components with respect to one another may be relevant as part of the position data, for example, a position angle in the case of an ability of a C-arm to displace in an outer arm by a holder (carriage).

In this context, reference is also to be made to the fact that in exemplary embodiments in general, but also specifically for the case of a cable routing element that includes a grooved hose between cable outlets, a more precise description is possible due to the use of rigid segments that are coupled in the kinematic chain. For example, a grooved hose may thus be modelled by multiple segments, which are rotationally coupled to one another, in order also to achieve an improvement here. In the case of X-ray facilities having a C-arm that is guided in an outer arm, in particular via a holder (carriage) as a carrier component, which the cable outlet is fastened to, it has been shown however as stated that the contribution to the collision risk and to the limitation of the freedom of movement by the grooved hose is to be evaluated as rather low in comparison to the cable outlets with the result that in such a case the outlay of additional modelling segments is not inevitably necessary. Other cases may however exist in which this is also shown to be expedient for a clear gain in freedom of movement for the functional component.

As a further possibility for taking into consideration the grooved hose, it is also possible to use a model, which is enlarged locally, in particular along an edge around a cylindrical shape, of a patient couch (therefore the patient table surface of a patient table) of the X-ray facility. Here, excellent results have been shown with dedicated combination of a modelling of the cable outlets with such a local enlargement of the model representation of the patient couch, wherein the patient couch is used in particular as the object or part of a or the object with which collisions are to be prevented. The local enlargement of the patient couch is then not used generally, but rather only in relation to the modelled cable outlets. In other words, this means that a collision monitoring between the patient couch and the cable outlets uses the local enlargement however all other movement paths, in particular the other objects and components of the X-ray facility remain unimpaired by the local enlargement. The freedom of movement is thus not limited but rather is even expanded in relation to feasible approaches, which map the additional component entirely (here therefore grooved hose and cable outlets) as an expansion of the patient couch model.

The medical technology facility may be an X-ray facility having a recording arrangement that includes an X-ray emitter and an X-ray detector as a functional component. X-ray facilities of this type are frequently used during medical interventions. Owing to the plurality of medical procedures in which such X-ray facilities are useful, it is advantageous if a particularly high number of clinically relevant positions of the functional component, here therefore recording geometries, may be reached in the shortest path. The present disclosure may therefore be used with particular advantage on X-ray facilities of this type as medical facilities.

The at least one carrier component may be a C-arm that is guided in a displaceable manner in an outer arm via a holder, in particular a carriage, as a further carrier component and the position of the C-arm with respect to the holder is described in the position data by a position angle. The relationship for an element, e.g., a cable outlet of a cable from the holder to the cable routing component that as an additional component guides the functional component that is arranged on the C-arm, allocates the additional data, in particular an angular position of the cable outlet that is modelled as a rigid element, to the position angle. In this case, the C-arm is guided via a holder (for example, a carriage), which is a carrier component, in the outer arm because the arm length of the (inner) C-arm and the outer arm (outer telescopic C-arm) differ greatly. The holder may in this case move with a different (but fixed) translation ratio in the two arms. In this case, it may also be provided that in the case of a cable routing component that is fastened to the C-arm and the holder that displaceably connects the C-arm to the outer arm, the additional data describes an angular position of the respective cable outlets as additional components to the respective carrier component (C-arm, holder).

In a specific exemplary embodiment of this type, a deterministic relationship between the angular position of the cable outlets and the position angle of the C-arm is thus used, which exists owing to the grooved hose of fixed length and consistent mechanical characteristics between X-ray facilities of this type having C-arms. Owing to the defined mechanical coupling by the holder, it is also possible to use the orbital angle (position angle between the outer arm and C-arm) as the position angle, which then also describes the position of the C-arm and holder with respect to one another. In this case, it is possible to perform a modelling of the cable outlets as kinematic elements having rotational angles that depend solely on known position angles, e.g., the orbital angle. Using the additional information obtained by the relationship solves the uncertainty and the cable outlet model may be reduced to its actual geometric form. In this case, the broadened kinematic configuration may expediently map the cable outlet movement due to new rotatably coupled model elements in the Denavit-Hartenberg notation (DH notation). These elements are integrated as additional components expediently in a minimally invasive manner into the movement chain for the modelling of the carrier arrangement. The angular positions of the cable outlets that are determined from the relationship are introduced into the kinematic chain in order to trigger an update of the movement model so as to render it possible to accurately calculate spacing.

In certain embodiments, the relationship may be stored as a look-up table, wherein the modelling unit is configured so as to determine by interpolation additional data for values of the position data which lie between table values in the look-up table. It is feasible in a manner that is simple to implement to store the relationship, for example, on the basis of results of a calibration measurement, as a look-up table in a storage the control facility for the modelling unit. In other exemplary embodiments, it may naturally also be feasible to store the relationship as a mathematical function that is determined, for example, by a fit. In the case of a look-up table, it is particularly advantageous if an interpolation takes place for values of the position data, which lie between table values of the look-up table, in order to determine the corresponding additional data. In this case, linear interpolation may be used.

In order to determine at least one part of the position data, the medical technology facility may have at least one encoder that is allocated to an actuator. It is particularly advantageously possible to entirely omit additional sensor systems for determining position data. In this case, the prevailing position of the actuators and consequently the carrier components with respect to one another may be tracked in the control facility of the medical technology facility. Additionally, it is possible to use the corresponding encoder feedback of the actuators for the tracking.

The collision protection of the collision protection system may relate to the patient as the subject, which, for example in cylindrical modelling may be brought into the movement model, because their positioning, which may be more precisely determined from procedure data, on a patient couch that is allocated to the medical technology facility may be known, just as the patient couch or the entire patient table, which may be considered as an object with which collisions are to be prevented, is likewise tracked in the control device, for example, with regard to its actuators and adjustment possibilities. Consequently, a patient table having a patient couch may be inserted into the movement model as at least one object and also the patient may be inserted as the subject in a particularly simple manner without complex additional sensor systems and the like. The detection unit may therefore be designed so as to use as a subject at least one patient, in particular who is at least in part modelled as cylindrical, and/or to use as an object a patient table that in particular forms a part of the medical technology facility. Furthermore, other objects and/or subjects may be taken into consideration in the movement model as long as these objects and/or subjects may be mapped in a simple manner expediently in a corresponding pose that at least approaches reality.

In the embodiment as an X-ray facility, for other medical technology facilities, the carrier arrangement may be mounted on the ceiling. Mounting the carrier arrangement on the ceiling provides a larger free space in the region near to the floor for devices, people, and their movement, which may be expedient with regard to medical interventions, for example, minimally invasive interventions. However, naturally a floor mounted carrier arrangement is also feasible.

A signal that indicates the possibly impending collision may be output as a collision protection measure. As a collision protection measure, it may also be provided, for example, to slow down and/or to stop the movement of at least one carrier component and/or to output a warning and/or an alternative travel path to reach a destination position of the functional component.

In addition to the medical technology facility, the disclosure also relates to a computer-implemented method for operating a medical technology facility, wherein the medical technology facility includes: at least one functional component; a carrier arrangement, which is provided so as to position the functional component in the space and includes at least two carrier components that may be moved relative to one another; at least one additional component that may be positioned and/or formed differently in different positions of the carrier arrangement; and a control facility for collision protection. The computer-implemented method includes: using position data that indicates prevailing positions of the carrier components so as to update a digital movement model of the medical technology facility; using the digital movement model to map the carrier components and the functional component with their movability; evaluating the prevailing movement model so as to detect possibly impending collisions with at least one subject and/or object that is located in the movement region and that is mapped in the movement model; and performing at least one collision protection measure when a possibly impending collision is detected. In the computer-implemented method, the movement model also maps the movement of the additional component, wherein additional data that describes a prevailing pose and/or shape of the additional component is determined from a relationship, which is stored in the control facility, of at least one part of the position data with the additional data.

All the embodiments in relation to the medical technology facility may be transferred in a similar manner to the computer-implemented method with the result that it is also possible to obtain the already mentioned advantages using this method.

A computer program may be directly loaded into a storage device of a control facility of a medical technology facility and may have program code configured to perform the acts of a method disclosed herein when the computer program is executed on the control facility. The computer program may be stored in an electronically readable data carrier, which therefore includes control information that is stored thereon. The control information includes at least one computer program and is configured, when the data carrier is used in a control facility of a medical technology facility, to form this computer program so as to implement the method disclosed herein.

BRIEF DESCRIPTION OF THE DRAWINGS

Further advantages and details of the present disclosure are evident in the exemplary embodiments described below and also with the aid of the drawings. In the drawings:

FIG. 2 depicts an example of the functional structure of a control facility of the X-ray facility.

FIG. 3 depicts an example of a mapping of a first cable outlet in a movement model.

FIG. 4 depicts an example of a mapping of a second cable outlet in the movement model.

DETAILED DESCRIPTION

Figure 1:
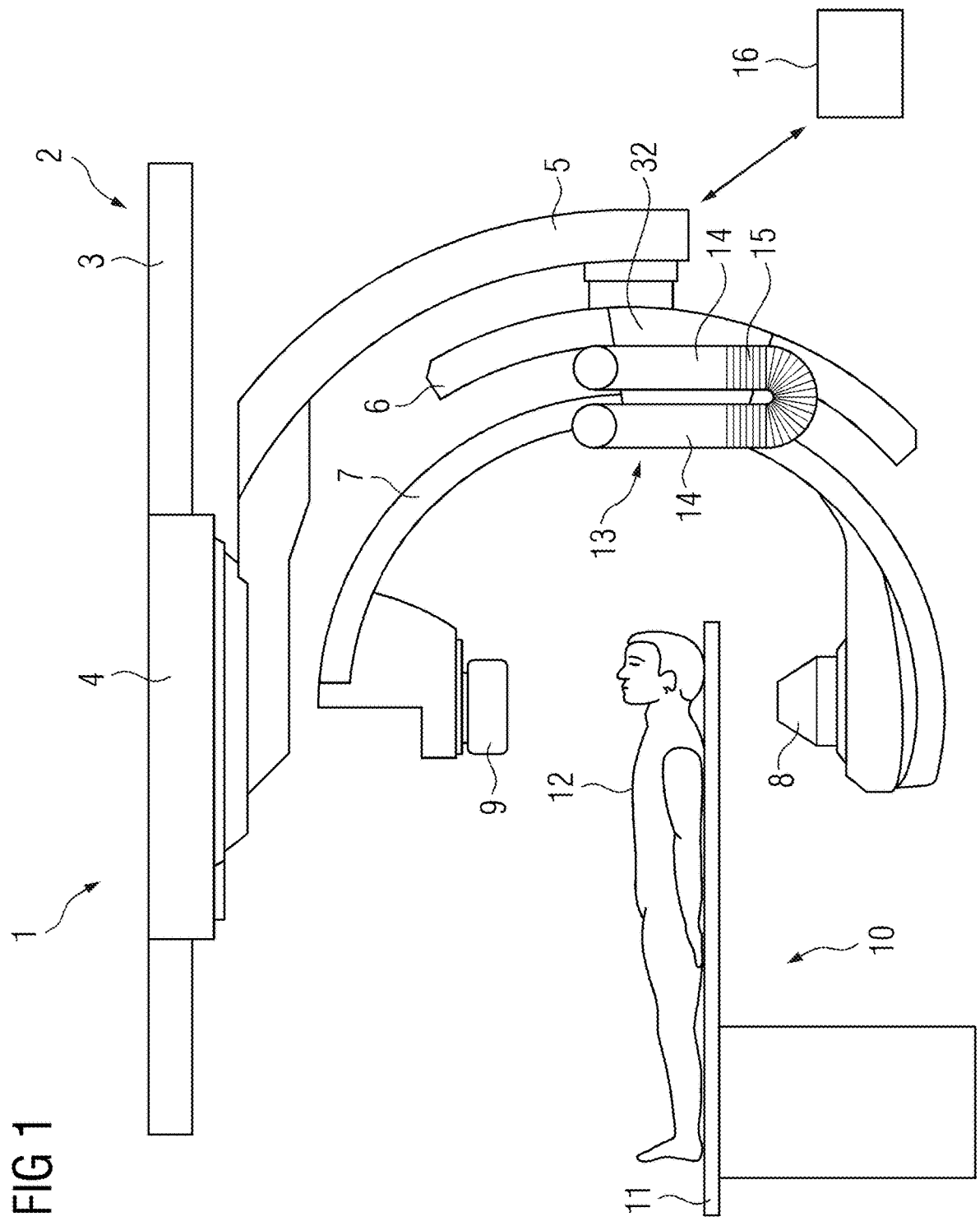
FIG. 1 depicts a schematic sketch of an example of a medical technology facility, which is configured as an X-ray facility.

FIG. 1 illustrates, as an exemplary embodiment of a medical technology facility, an X-ray facility 1 that in the present case has a ceiling mounted carrier arrangement 2 having multiple carrier components that may be moved relative to one another so as to produce different degrees of freedom of movement. For example, the carrier arrangement 2 includes a carrier plate 4 that may be moved in a rail system 3 and an arm 5 is rotatably fastened to this carrier plate and in turn an outer arm 6 is rotatably arranged on the arm 5 and a C-arm 7 is displaceably mounted in the outer arm 6 so as to set an orbital angle by a holder 32, for example, a carriage. Owing to the different arm lengths of the C-arm 7 and the outer arm 6, the holder moves with a different, fixed translation ratio in the two arms 6, 7. An X-ray emitter 8 and an X-ray detector 9 are arranged lying opposite one another on the C-arm 7 so as to form a recording arrangement as a functional component.

The X-ray facility 1 moreover includes a patient table 10, which is only indicated schematically here, having a patient couch 11 for a patient 12. During a medical procedure, (e.g., during an examination and/or treatment), it is possible to record X-ray images from different positions of the recording arrangement, in particular, different recording geometries.

In this case, cables for electrical power supply and/or data communication with the X-ray emitter 8 and the X-ray detector 9 are initially guided in a concealed manner by the arm 5 and then via a flexible grooved hose, which is not collision relevant, to the holder 32 on the outer arm 6. Owing to the displaceability of the holder 32 and C-arm 7 with respect to one another, a cable routing component 13 is used in order to further guide the cable to the C-arm 7. The cable routing component 13 includes two rigid cable outlets 14 that are rotatably arranged on the respective carrier component. Therefore, the holder 32 and the C-arm 7 and the cable outlets are connected via a flexible grooved hose 15. If the C-arm 7 is displaced in the holder 32, the angular positions of the cable outlets 14 change with respect to the holder 32 or the C-arm 7 and the grooved hose 15 deforms.

The operation of the X-ray facility 1 is controlled by a control facility 16 having at least one processor and at least one storage device that is also designed so as to implement the method.

In particular, a collision protection system is formed in the control facility 16 that uses a movement model in which the cable outlets 14 are also mapped as additional components, here rotatably coupled rigid elements, as is explained more precisely in detail below.

FIG. 2 initially illustrates a schematic sketch of the functional construction of the control facility 16. In addition to the already mentioned storage device 17 and further function units, wherein purely in an exemplary manner a recording unit 18 is illustrated, the collision protection system 19 initially has at least one modelling unit 20. The modelling unit 20 uses prevailing position data of the carrier arrangement 2, which is provided to the control facility 16 via an interface by encoders that are allocated to corresponding actuators for the degrees of freedom of movement and are not further illustrated in FIG. 1, in order to update a movement model of the X-ray facility 1 in which the patient 12 is also mapped as the subject, (e.g., as a cylinder), where necessary with additional safety zones. In this case, the carrier components may be mapped as part of a dynamic chain in a manner that is not particularly complex and is simple to manage.

In the present case, the kinematic configuration is broadened via the carrier arrangement 2 because the cable outlets 14 have also been added as additional components and the virtual representation of the cable outlets as rigid model elements that are rotatably coupled to the respective carrier component, here the holder 32 and the C-arm 7, in Denavit-Hartenberg notation (DH notation).

This is further explained by FIGS. 3 and 4 that illustrate schematically in each case sections of the movement model 21 that are limited for the sake of clarity to the respective carrier component and additional component that is kinematically coupled to the carrier component, in other words the respective cable outlet 14. FIGS. 3 and 4 illustrate with solid lines the kinematic elements 22 that represent the cable outlets 14 in a zero position 23 that corresponds to an angular position of 0°. The kinematic element 22 is rotatably coupled about an axis of rotation 24, which extends perpendicular to the image plane, to the respective carrier component (holder 32/C-arm 7) or the model element that represents this carrier component. A further angular position 25 having the corresponding direction 26 in which the angle is described is indicated as dashed.

The cable outlets 14 are modelled as kinematic elements 22 that are rotatable in relation to the respective carrier element with the result that it is not necessary to provide an enlarged mapping in dependence upon their fundamental movability, but rather it is possible to perform a reduction to the actual geometric shape. Owing to the integration into the kinematic chain by the DH notation, a minimally invasive integration into the movement model 21 is realized. In this example, the rigid, easily mappable cable outlets 14 are incorporated into the movement model 21 because it has been shown that these are mainly relevant for the collision protection and a broadening of the freedom of movement for the recording arrangement as the functional component. Exemplary embodiments are however feasible in which a modelling of the grooved hose 15 is performed, for example, by rotatably connected rigid part segments.

In order to also be able to update the movement model 21 in relation to the movement of the cable outlets 14, it is necessary to determine the angular position 25 of the cable outlets. Here it has been shown that a deterministic relationship exists between a part of the position data, here specifically the orbital angle, and the angular position 25 (as additional data that relates to the additional component). The orbital angle is thus used as a position angle that describes the position of the C-arm 7 with respect to the holder 32. The relationship may be determined in a calibration measurement and render it possible purely from knowing the orbital angle, which may indeed be determined from data of at least one encoder of the associated at least one actuator, to also determine the angular position 25 of the respective cable outlet 14, defined in accordance with FIG. 3 and FIG. 4. The angular positions 25 of the cable outlets 14 are then introduced into the kinematic chain in order to trigger an update of the movement model 21.

Figure 5:
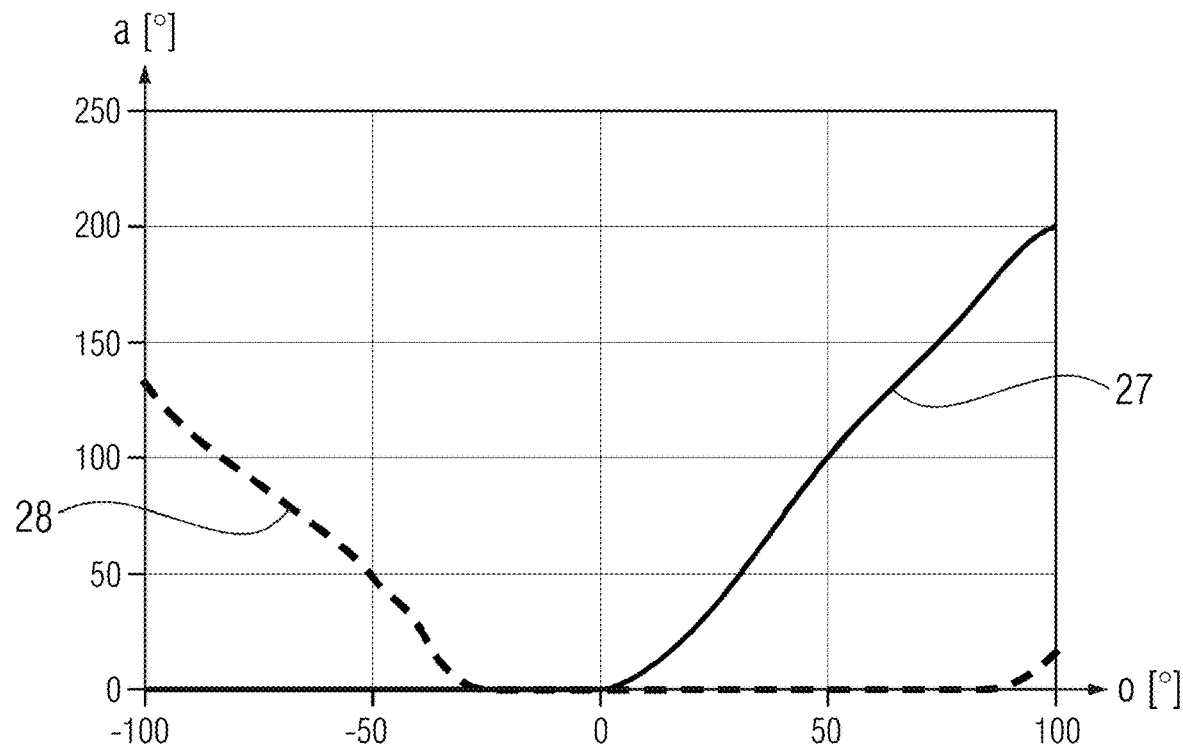
FIG. 5 depicts a graph, which illustrates an example of a relationship between position data and additional data.

FIG. 5 illustrates a relationship of this type in an exemplary manner with the aid of a graph in which the respective angular position is plotted as an angle (a) against the orbital angle (o). In this case, the curve 27 illustrates the angle that is illustrated in FIG. 3 with respect to the C-arm 7, the curve 28 illustrates the angle that is explained in FIG. 4 with respect to the holder 32. The curves 27, 28 may be obtained from a calibration measurement.

The relationship may be stored as a look-up table 29, cf. FIG. 2, in the storage device 17. In this look-up table 29, various table values of the orbital angle are allocated corresponding angular positions 25, with the angles (a and o) of the two cable outlets 14. The modelling unit 20 may be configured to find allocated intermediate positions by in particular linear interpolation for values of the orbital angle that lie between the table values.

Furthermore, in relation to FIG. 2, the collision protection system 19 moreover has a detection unit 30 that evaluates the prevailing movement model 21 and where necessary as a movement sequence also the movement model over a timespan in the past in order to check whether collisions may be impending. In this case, the patient 12 and also the patient table 10 may be considered as potential collision objects. In particular, in this case spacings or spacing curves between carrier components and functional components with respect to this subject or the objects of the patient table 10 may be taken into consideration. Additionally, in certain examples where applicable, penetration depths may also be estimated. When a possibly impending collision is detected, an intervention unit 31 performs at least one collision protection measure. This may be in the form of outputting a signal that indicates the possibly impending collision. The collision protection measure may also include braking, stopping, and/or evading and also outputting warnings or information.

Embodiments that are fundamentally known in the art may be selected for the detection unit 30 and the intervention unit 31.

Figure 6:
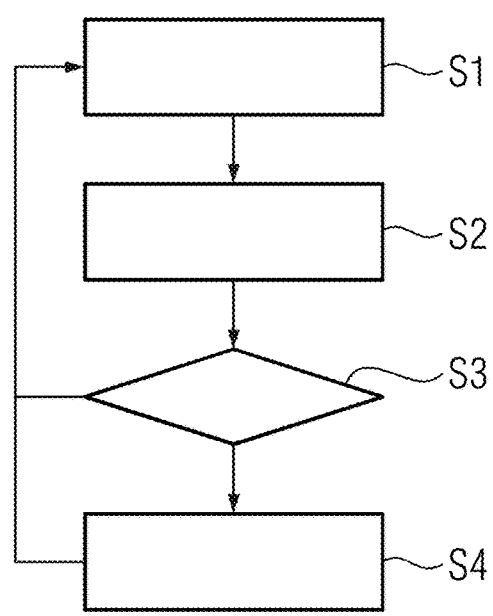
FIG. 6 depicts a flowchart of an example of the method.

Finally, FIG. 6 illustrates a flowchart of an exemplary embodiment of the method as may be implemented by the control facility 16. In this case, in act S1, the movement model 21 is continuously updated with the aid of the position data by the modelling unit, wherein the relationship between at least one part of the position data, in particular the orbital angle, with the additional data, here the angular positions 25, is used in order to determine the prevailing angular positions 25 of the cable outlets 14 and to update not only in relation to the carrier arrangement 2 but rather also in relation to the cable outlets 14, as described.

As is already mentioned, the updating of the movement model 21 may take place whenever new position data is available, in particular, triggered by a change or also cyclically.

In act S2, a check is then performed by the detection unit 30 as to whether a collision is impending, here with the patient 12 or the patient table 10.

If, in act S3, it is established that a collision has been detected, in act S4, corresponding collision protection measures are introduced as described by the intervention unit 31.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical technology facility comprising:
   at least one functional component;
   a carrier arrangement configured to position the functional component in a space, wherein the carrier arrangement comprises at least two carrier components configured to be moved relative to one another;
   at least one additional component positioned and/or formed differently in different positions of the carrier arrangement; and
   a control facility configured to form a collision protection system, wherein the control facility comprises:
      a modelling unit configured to update a digital movement model of the medical technology facility, wherein the digital movement model maps the at least two carrier components and the at least one functional component with a movability of the at least two carrier components and the at least one functional component based on position data that indicates prevailing positions of the at least two carrier components;
      a detection unit configured to evaluate the digital movement model so as to detect possibly impending collisions with at least one subject and/or object that is located in a movement region and mapped in the digital movement model; and
      an intervention unit configured to implement at least one collision protection measure when a possibly impending collision is detected,
      wherein the digital movement model also maps a movement of the at least one additional component,
      wherein the modelling unit is configured to determine additional data that describes a prevailing pose and/or a shape of the at least one additional component from a relationship of at least one part of the position data with the additional data, and
      wherein the relationship is stored in the control facility.

2. The medical technology facility of claim 1, wherein the at least one additional component comprises at least one element of a cable routing component for at least one cable.

3. The medical technology facility of claim 2, wherein the at least one element of the cable routing component comprises at least one rigid cable outlet, in particular for connecting to a grooved hose.

4. The medical technology facility of claim 1, wherein the additional component is added to the digital movement model that uses at least one kinematic chain in Denavit-Hartenberg notation, in particular as a rigid, rotatably coupled kinematic element.

5. The medical technology facility of claim 4, wherein the additional data describes an angular position of the at least one kinematic chain.

6. The medical technology facility of claim 1, wherein the medical technology facility is an X-ray facility comprising a recording arrangement as a functional component, which comprises an X-ray emitter and an X-ray detector.

7. The medical technology facility of claim 6, wherein at least one carrier component of the at least two carrier components of the carrier arrangement is a C-arm that is guided in a displaceable manner in an outer arm via a holder as a further carrier component,
   wherein a position of the C-arm with respect to the holder is described in the position data by a position angle,
   wherein the relationship for an element, in particular a cable outlet, of a cable from the holder to a cable routing component, which as an additional component guides the functional component and, arranged on the C-arm, allocates the additional data to the position angle.

8. The medical technology facility of claim 7, wherein the cable routing component is fastened to the C-arm and the holder, and
   wherein the additional data describes an angular position of a respective cable outlets as additional components to a respective carrier component of the at least two carrier components.

9. The medical technology facility of claim 1, wherein the relationship is configured to be stored as a look-up table, and
   wherein the modelling unit is configured to determine by interpolation additional data for values of the position data that lie between values in the look-up table.

10. The medical technology facility of claim 1, further comprising:
    at least one encoder allocated to an actuator,
    wherein the at least one encoder is configured to determine at least one part of the position data.

11. The medical technology facility of claim 1, wherein the detection unit is configured to use as a subject at least one patient, in particular who is at least in part modelled as cylindrical, and/or to use as an object a patient table that in particular forms a part of the medical technology facility.

12. A computer-implemented method for operating a medical technology facility having at least one functional component, a carrier arrangement that positions the at least one functional component in a space and comprises at least two carrier components configured to be moved relative to one another, and at least one additional component positioned and/or formed differently in different positions of the carrier arrangement, the computer-implemented method comprising:
    updating, by a control facility of the medical technology facility, a digital movement model of the medical technology facility using position data that indicates prevailing positions of the at least two carrier components of the carrier arrangement, wherein the digital movement model maps the at least two carrier components and the at least one functional component with a movability of the at least two carrier components and the at least one functional component;

evaluating, by the control facility, the digital movement model so as to detect a possibly impending collision with at least one subject and/or object that is located in a movement region and mapped in the digital movement model; and performing, by the control facility, at least one collision protection measure when the possibly impending collision is detected, wherein the digital movement model also maps a movement of the at least one additional component, wherein additional data that describes a prevailing pose and/or a shape of the at least one additional component is determined from a relationship, which is stored in the control facility, of at least one part of the position data with the additional data.

13. A computer program that, when executed on a control facility, is configured to:

update a digital movement model of a medical technology facility using position data that indicates prevailing positions of at least two carrier components of a carrier arrangement of the medical technology facility, wherein the digital movement model maps the at least two carrier components and at least one functional component of the medical technology facility with a movability of the at least two carrier components and the at least one functional component;

evaluate the digital movement model so as to detect a possibly impending collision with at least one subject and/or object that is located in a movement region and mapped in the digital movement model; and perform at least one collision protection measure when the possibly impending collision is detected, wherein the digital movement model also maps a movement of at least one additional component, wherein additional data that describes a prevailing pose and/or a shape of the at least one additional component is determined from a relationship, which is stored in the control facility, of at least one part of the position data with the additional data.

* * * * *